United States Patent [19]

Hayashi et al.

[11] Patent Number: 5,276,503

[45] Date of Patent: Jan. 4, 1994

[54] METHOD AND APPARATUS FOR GAS PHASE SYNTHESIS

[75] Inventors: Yasuaki Hayashi; Yukinobu Hibino, both of Tsukuba, Japan

[73] Assignee: Ninon Shinku Gijutsu Kabushiki Kaisha, Kanagawa, Japan

[21] Appl. No.: 786,208

[22] Filed: Oct. 31, 1991

[30] Foreign Application Priority Data

Nov. 5, 1990 [JP] Japan .................. 2-297167
Oct. 9, 1991 [JP] Japan .................. 3-262318

[51] Int. Cl.$^5$ .................. G01J 4/00; B05C 11/00
[52] U.S. Cl. .................. 356/369; 250/225; 118/665; 118/712
[58] Field of Search ............ 356/364, 365, 366–370, 30, 36, 37; 250/225; 118/665, 712; 427/38, 39, 45.1, 162, 249, 307, 309; 423/446

[56] References Cited

U.S. PATENT DOCUMENTS

| | | | |
|---|---|---|---|
| 3,819,948 | 6/1974 | Iijima et al. | 118/665 |
| 3,941,482 | 3/1976 | Schneider | 356/30 |
| 4,332,833 | 6/1982 | Aspnes et al. | |
| 4,906,844 | 3/1990 | Hall | 356/369 |
| 4,925,701 | 5/1990 | Janben et al. | 427/38 |
| 5,006,203 | 4/1991 | Purdes | 427/38 |
| 5,091,320 | 2/1992 | Aspnes et al. | 356/369 |

FOREIGN PATENT DOCUMENTS

WO87/05700 9/1987 PCT Int'l Appl.

OTHER PUBLICATIONS

"Vapor Deposition of Diamond Particles from Methane", by Matsumoto, Seiichiro et al., *Japanese Journal of Applied Physics*, vol. 21, pp. L183–L185, Mar. 1982.

"Diamond Synthesis from Gas Phase in Microwave Plasma", by Kamo, Mutsukazu et al., *Journal of Crystal Growth* 62, pp. 642–644 (Apr. 1983).

"Growth of diamond think films by dc plasma chemical vapor deposition", by Suzuki, Kazuhiro et al., *Applied Physics Letters*, 50, pp. 728–729 (Jan. 1987).

"Ellipsometry and Polarized Light", by Azzam, R. M. A. et al, North-Holland Publishing Company, pp. 269–289 (1987).

Drevillon. *Thin Solid Films*, 130, 165, Apr. 1985.

Thin Solid Films; vol. 181, 10 Dec. 1989, pp. 565–578; R. W. Collins et al. 'Real-time and spectroscopic ellipsometry of diamond and diamond-like carbon' abstract.

Applied Physics Letters; vol. 52, no. 24, 13 Jun. 88,; pp. 2025–2027 R. W. Collins 'Surface, interface, and bulk properties of amorphous carbon films characterized by in situ ellipsometry'.

Journal of Materials Research; vol. 5, no. 11, Nov. 1990, pp. 2531–2537 A. Grill et al. 'Optical and Tribological Properties of Heat-Treated Diamond–like carbon'.

*Primary Examiner*—Richard A. Rosenberger
*Assistant Examiner*—Hoa Q. Pham
*Attorney, Agent, or Firm*—Armstrong, Westerman, Hattori, McLeland & Naughton

[57] ABSTRACT

A method of gas phase synthesis including the steps of measuring, by ellipsometry, optical properties of a surface of a sample on which a film is formed during formation of the film, and of evaluating the density of nucleation from changes in ellipsometric parameter angles during formation of of the film. An apparatus for gas phase synthesis includes a synthesizing chamber, a light source means which is disposed outside the synthesizing chamber for radiating polarized light into the synthesizing chamber, a light-inlet window mounted on the synthesizing chamber for introducing thereinto the light radiated from the light source means, a light-outlet window mounted on the synthesizing chamber for leading the light introduced from the light-inlet window and reflected from a substrate on which a film is being formed out of the synthesizing chamber, a light-receiving means for receiving the light reflected from the substrate and passed through the light-outlet window, and a data processing system for receiving an output signal from the light-receiving means for measuring and analyzing a density of nucleation.

7 Claims, 6 Drawing Sheets

FIG_1

$N = 4 \times 10^9 /cm^2$

FIG. 2(c)

$N = 9 \times 10^9 /cm^2$

METHOD AND APPARATUS FOR GAS PHASE SYNTHESIS

BACKGROUND OF THE INVENTION

This invention relates to a method and apparatus for gas phase synthesis and, in particular, to a method of synthesizing in gas phase a functional material or a hard film, especially a diamond film to be used for mechanical purposes and for semiconductor purposes, as well as to an apparatus for carrying out this method.

As a representative example of a conventional apparatus for gas phase synthesis of a diamond film, there are known those as disclosed by S. Matsumoto et al in the Japanese Journal of Applied Physics, vol. 21, p. L183 (1982); M. Kamo et al in the Journal of Crystal Growth, 62, p. 642 (1983); K. Suzuki et al in the Applied Physics Letters, 50, p. 728 (1987).

In case the diamond film is used as a coating film on a tool or a wear-resistant sliding part, the adhesion of the film to a substrate is an important matter of interest. This matter is known to be solved by controlling or increasing the density of nucleation of the diamond crystal nuclei grown at the beginning on the substrate.

Further, in case the diamond film is used as a protection film on an optical window or a protection film of a lens, it is necessary for the film surface to be smooth in order to improve the light penetrating characteristics by minimizing the scattering of light on the film. However, since the diamond grows in the form of nuclei, the surface of the diamond film formed cannot be made smooth if the density of the nucleation is small. Therefore, in this case, it is also necessary to control or increase the density of nucleation of the diamond crystal nuclei.

In case the diamond film is used for semiconductor purposes, it is necessary to epitaxilly grow the diamond film. For this purpose, it is required that the film be formed under conditions of high density of growth of crystal nuclei, i.e., high density of nucleation.

As described above, controlling or increasing the density of nucleation is especially important in utilizing the material susceptible of easy nucleus growth such as diamond as a functional material or as a hard film.

On the other hand, it is sometimes disadvantageous from a viewpoint of other film characteristics or economy to unnecessarily increase the density of nucleation. In such a case, it is important to control the density of nucleation at a level above a predetermined value while satisfying the other requirements.

As a method of controlling or increasing the density of nucleation, there is known, at present, a method of scratching the substrate on which the film is formed with diamond powders prior to the film formation (as disclosed, for example, by Yugo et al in the Extended Abstracts of the 35th Spring Meeting of the Jpn. Soc. Appl. Phys. and the Related Societies, p. 438, 1988).

This method of scratching treatment with diamond powders is a method in which prior to film formation a substrate is placed into a solution containing therein diamond powders outside a synthesizing apparatus and subject it to ultrasonic vibrations for a predetermined period of time, or the substrate is rubbed against diamond powders to form very fine scratches on the substrate. Thereafter, the film is formed on the substrate. According to this method, by controlling the density of the scratches to be formed on the substrate, the density of nucleation can be controlled to a certain degree within a range of $10^5$ to $10^9/cm^2$.

The evaluation of the density of nucleation of the diamond nuclei has generally been made by taking out a sample, after film formation, to examine with an electron microscope or the like, thereby counting the number of grown nuclei within a predetermined area.

Since the control or the evaluation of the density of nucleation according to the conventional method is carried out only before or after the film formation, the grasping of the density of nucleation is nothing but an estimate or a result. Therefore, it was impossible in the conventional method to accurately control the density of nucleation.

Further, in case the number of grown nuclei is counted in process with an electron microscope, the electron microscope must be placed inside an apparatus for gas phase synthesis. It is impossible to count the number in such a high-pressure zone as in the method of gas phase synthesis because the mean free path of the electrons is short.

OBJECT AND SUMMARY OF THE INVENTION

Therefore, this invention has an object of providing a method of gas phase synthesis in which exact control of the density of nucleation can be carried out, as well as an instrument for carrying out the method.

The gas phase synthesizing method according to this invention is characterize by the steps of measuring, by ellipsometry, optical properties of a surface of a sample on which a film is formed during formation of the film, and of evaluating the density of nucleation from changes in ellipsometric parameter angles during forming of the film.

It is preferable to control the density of nucleation by adjusting film forming conditions during formation of the film.

It may also be so arranged that the density of nucleation is controlled by adjusting a temperature of the substrate.

The material to be synthesized is, for example, diamond.

The gas phase synthesizing apparatus according to this invention comprises a synthesizing chamber, a light source means which is disposed outside the synthesizing chamber for radiating polarized light into the synthesizing chamber, a light-inlet window mounted on said synthesizing chamber for introducing thereinto the light radiated from the light source means, a light-outlet window mounted on the synthesizing chamber for leading the light introduced from the light-inlet window and reflected from a substrate on which a film is being formed out of the synthesizing chamber, a light-receiving means for receiving the light reflected from the substrate and passed through the light-outlet window, and a data processing system for receiving an output signal from said light-receiving means for determining the density of nucleation.

The synthesizing chamber may further comprise a vacuum exhausting system connected thereto, a substrate electrode having a cooling circuit for maintaining the substrate to a predetermined temperature, and flow rate control means provided in the cooling circuit for adjusting an amount of cooling water through said cooling circuit.

The flow rate control means may be communicated with the data processing system.

In this invention, the polarized light such as laser light or the like is irradiated to the sample during the formation of the film to measure the changes in polarization before and after the reflection of the light on the film. These changes in the polarized light are representative of the optical or geometrical conditions of the surface of the sample. Since the differences in the density of nucleation appear as the differences in the geometrical shapes on the surface of the sample, it becomes possible to evaluate the density of nucleation by ellipsometry.

In addition, in ellipsometry, it is possible to dispose the light source means and the light-receiving means of the measuring system outside the synthesizing chamber of the gas phase synthesizing apparatus and to carry out the measurement only by admitting the light through the window into the synthesizing apparatus.

BRIEF DESCRIPTION OF THE DRAWINGS

The above and other objects and attendant advantages of this invention will become readily apparent by reference to the following detailed description when considered in conjunction with the accompanying drawings wherein:

FIG. 4 (a), (b) are explanation diagrams showing an equivalent multilayer film in carrying out simulated calculations;

DETAILED DESCRIPTION OF THE INVENTION

An embodying example of this invention gas phase synthesizing method and an instrument for carrying it out will now be explained with reference to the accompanying drawings.

Figure 1:
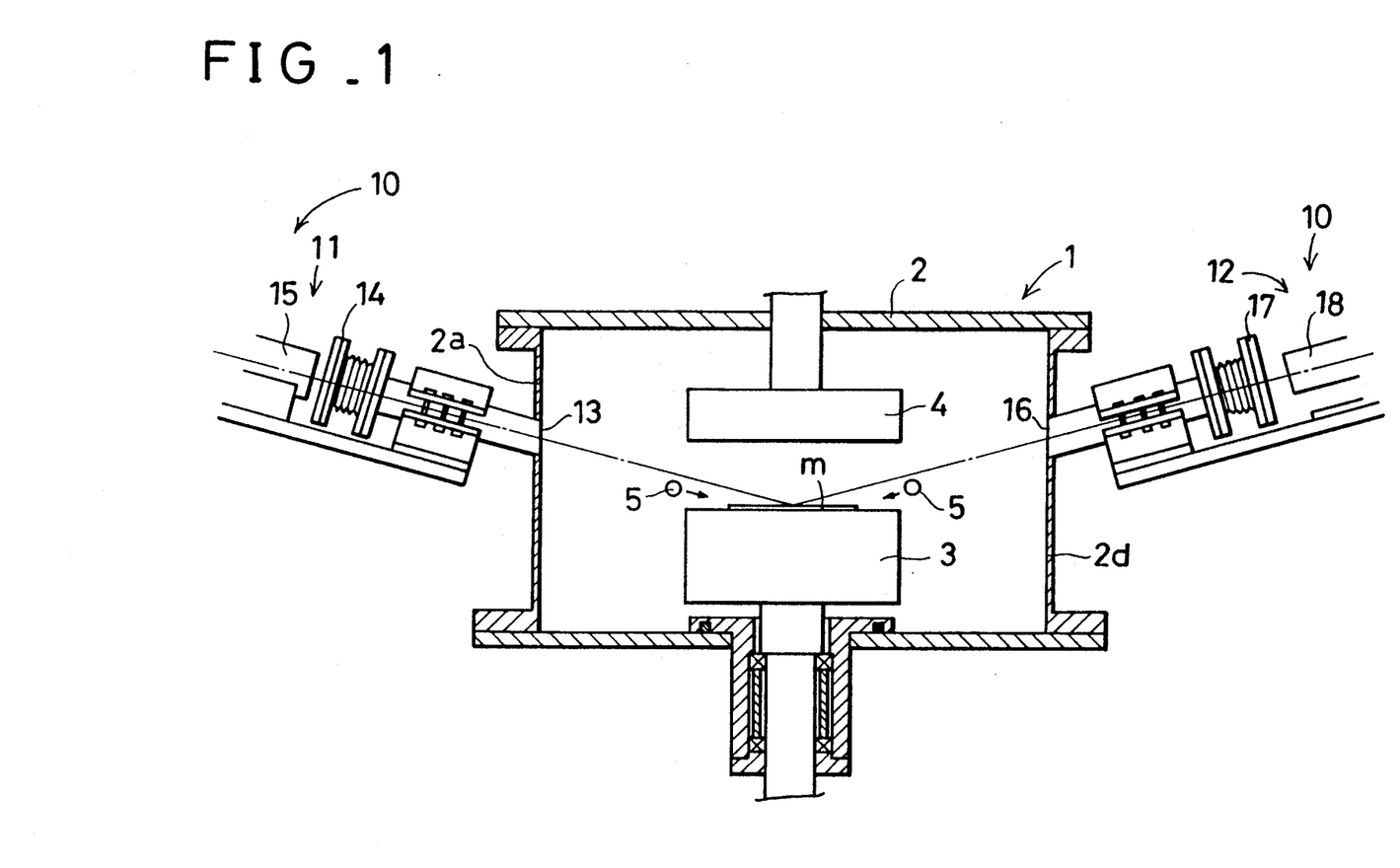
FIG. 1 is a sectional view of a gas phase synthesizing apparatus of one example of this invention.

FIG. 1 is an example of an apparatus for carrying out this invention method of gas phase synthesizing. Numeral 1 denotes an apparatus for gas phase synthesis.

This gas phase synthesizing apparatus 1 comprises a synthesizing chamber 2 for carrying out synthesizing therein. Inside this synthesizing chamber 2, a substrate electrode 3 is rotatably provided at a lower portion thereof and a discharging electrode 4 is provided at an upper portion thereof. In the neighborhood of the substrate electrode 3, there is provided a ring-like pipe 5 for introducing a reactive gas for diamond synthesis.

The gas phase synthesizing apparatus 1 is provided with an ellipsometer 10 for evaluating the density of nucleation of diamond crystal nuclei to be formed on a substrate m. This ellipsometer 10 is provided with a light source system 11 and a light receiving system 12. The light source system 11 comprises a light incident window 14, to function as a peep hole, which is provided in communication with an opening 13 which is formed in a side wall 2a of the synthesizing chamber 2, and a light source member 15 for emitting polarized laser light or the like for analyzing the surface of the substrate m. The light receiving system 12 comprises: a light emitting window 17, to function as a peep hole, which is provided in communication with an opening 16 which is located in a side wall 2b of the synthesizing chamber 2 at a position diametrically opposite to the side wall 2a and is formed on an optical axis of the light reflected from the substrate m; and a light receiving member 18 to receive the reflected light. Though not illustrated, the light receiving member 18 is connected to a data processing system for measuring and analyzing the changes in the polarization state of the light before and after reflection on the surface of the substrate m.

Next, a gas phase synthesizing method using the above-described gas phase synthesizing apparatus is explained hereinbelow.

Figure 2A:
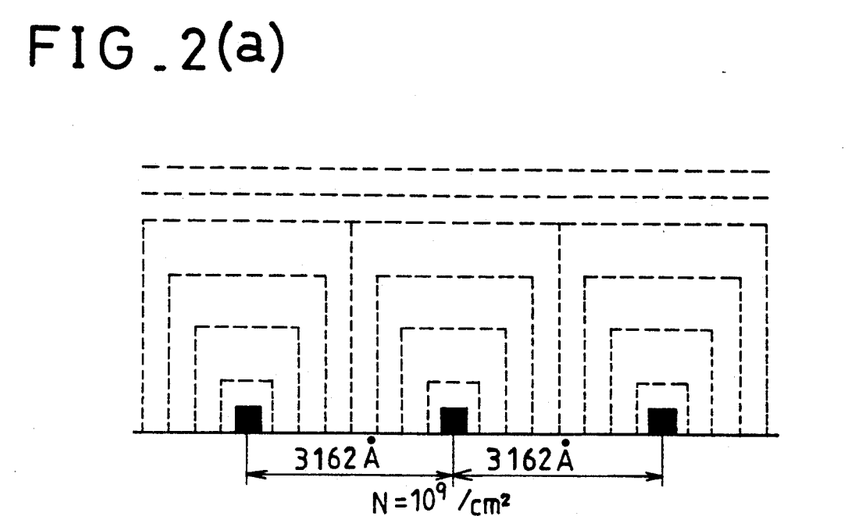
FIG. 2(a), (b), (c) are explanation diagrams showing nucleus growth and film formation with the change in density of nucleation.
Figure 2B:
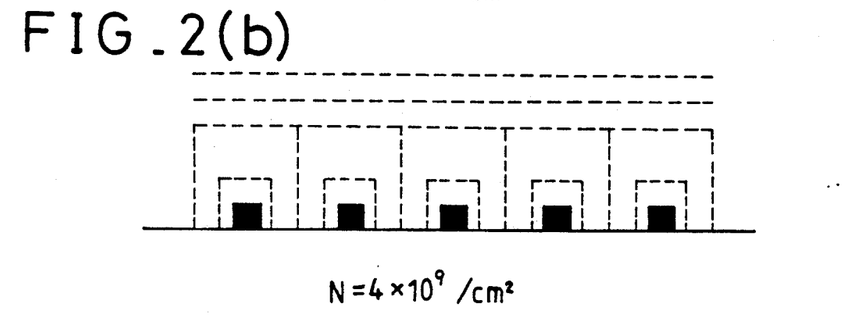
Figure 2C:
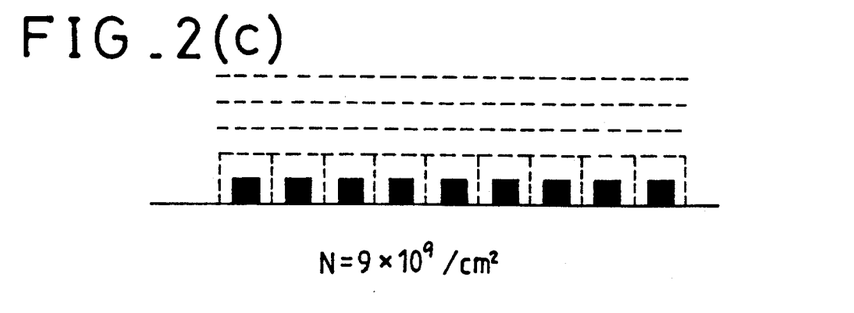

The evaluation of the density of nucleation by ellipsometry during the film formation was examined by simulating calculations. Silicon was used as the substrate m on which the film is formed. It is supposed that the film grows, as shown in FIG. 2(a), (b) and (c), in a condition in which the diamond nuclei formed on the substrate m keep on growing while maintaining their cubic shape until the neighboring nuclei collide with each other, thereby growing into a film. In FIG. 2(a), (b) and (c) there are shown, as can be clearly seen therefrom, examples of the density N of nucleation of $10^9/cm^2$, $4 \times 10^9/cm^2$ and $9 \times 10^9/cm^2$, respectively.

The ellipsometric simulating calculation can be performed as follows.

Figure 4A:
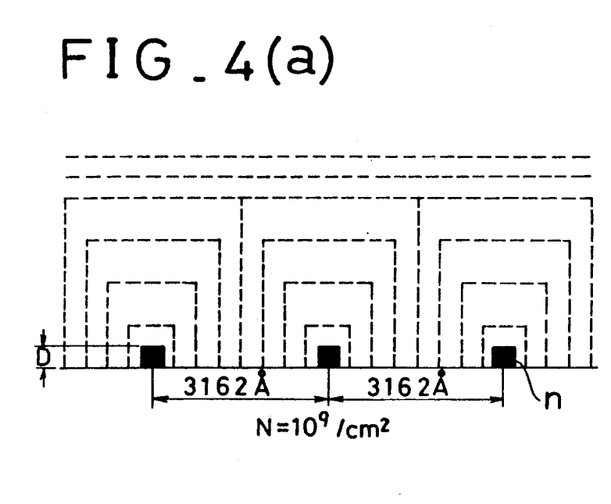
Figure 4B:
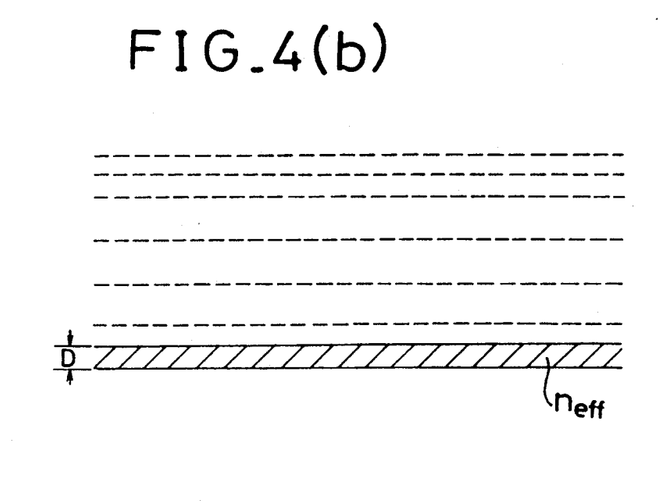

First, even though the grown diamond is in the form of nuclei, if the wave length of the light to be measured is in the length of several times the distance between the nuclei, an effective medium approximate calculation can be applied; the grown diamond can be treated in the same way as a homogeneous film. In other words, where N is the density of nucleation, n is the refractive index of the bulk diamond, D is the length of one side of each diamond nucleus of cubic shape, the effective refractive index $n_{eff}$ of a homogeneous film having a thickness of D can be expressed by the following formula (see FIG. 4(a) and (b)):

$$\frac{n_{eff}^2 - 1}{n_{eff}^2 + 2} = D^2 \cdot N \frac{n^2 - 1}{n^2 + 2}$$

The calculations of ellipsometry of equivalent homogenous single-layer film can be obtained by the following formula (see, for example, R. M. A. Azzam and N. M. Bashara, "Ellipsometry and Polarized Light", North-Holland Pub. Co., 1977):

$$\tan\Psi \cdot e^{i\Delta} = \frac{\frac{r_{1p} + r_{2p}e^{-2id}}{1 + r_{1p}r_{2p}e^{-2id}}}{\frac{r_{1s} + r_{2s}e^{-2id}}{1 + r_{1s}r_{2s}e^{-2id}}}$$

where $r_{1p}$ and $r_{2p}$ are Fresnel reflection coefficients of components p of polarized light, $r_{2s}$ and $r_{2s}$ are Fresnel reflection coefficients of components s of polarized light, $r_{1p}$ and $r_{1s}$ are Fresnel coefficients between vacuum and the equivalent single-layer film, $r_{2p}$ and $r_{2s}$ are Fresnel coefficients between the equivalent single-layer film and the substrate, e is a base of natural logarithm, i is $\sqrt{-1}$, and $\Psi$ and $\Delta$ are ellipsometric parameter angles.

Further, d can be obtained by the following formula:

$$d(\text{deg}) = \frac{360}{\lambda} D(n_{eff}^2 - \sin^2\phi)^{\frac{1}{2}}$$

where $\lambda$ is the wave length of the light and $\phi$ is the angle of incidence.

Figure 3:
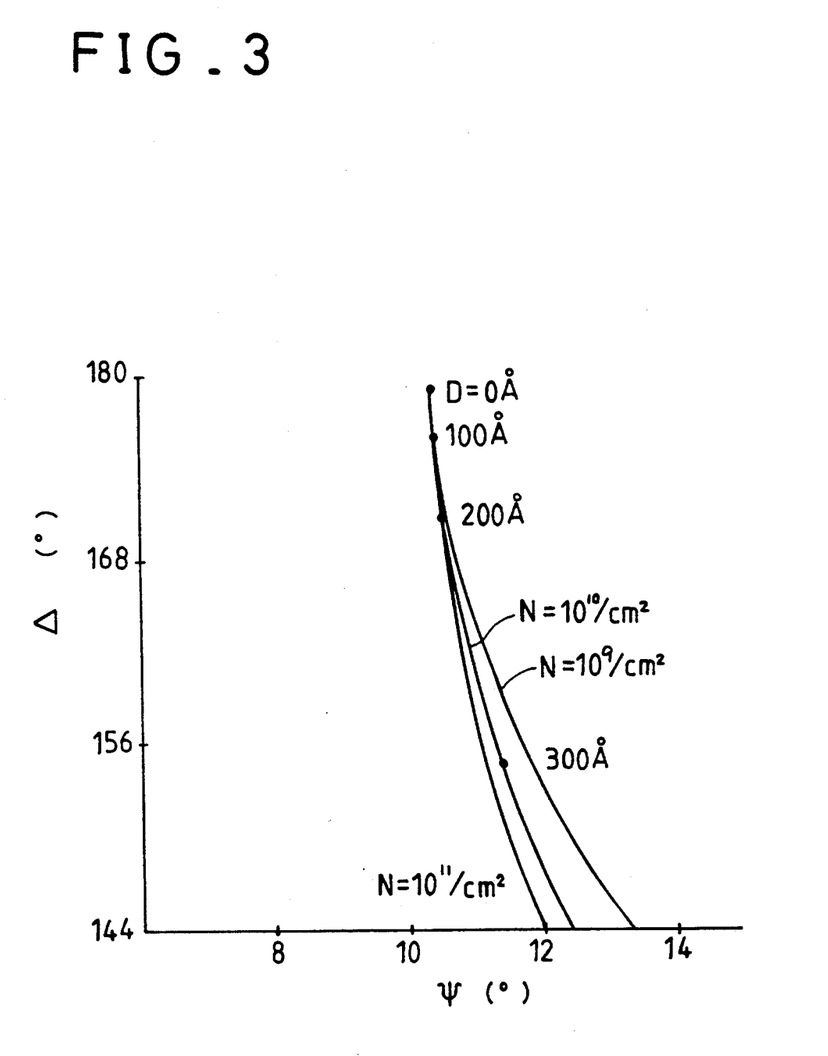
FIG. 3 is a graph showing the relationship between the density of nucleation and ellipsometric parameter angles.

FIG. 3 shows the changes in the ellipsometric parameter angles psi ($\Psi$) and delta ($\Delta$) in accordance with the growth of the diamond nuclei (i.e., the increase in D). Due to the difference in the density N of nucleation, the parameter angles $\Psi$ and $\Delta$ begin to show different changes. In other words, as the length D of one side of the nucleus which is supposed to be in cubic shape becomes larger, the difference becomes larger. When the accuracies of the parameter angles $\Psi$ and $\Delta$ are supposed to be 0.1°, it is possible to evaluate in which order the density of nucleation lies in D less than 300 Å in case of $N=10^{10}/cm^2$.

Next, an explanation will be made about the actual forming of a film. By DC discharging, 0.2-5% methane gas diluted by hydrogen was decomposed. A silicon wafer was placed as a substrate m on the substrate electrode 3. During the formation of the film, the surface of the substrate m was observed by an ellipsometer 10. The film forming conditions were changed within a range of substrate temperature of 400° to 1000° C., a reaction pressure of 1 to 40 kPa and a discharging electric current of 2 to 10 A/cm$^2$. The film forming operation was continued while trying to find out a condition in which the density of formation of diamond crystal nuclei (i.e., density of nucleation) became maximum. As a result, it was possible to grow the diamond crystal nuclei at a high density of $10^9$ to $10^{10}$/cm$^2$ without the treatment of scratching the silicon substrate. This value of the density of nucleation was found to agree with the result of electron microscope examination within a range of 100 to 200%.

Figure 5:
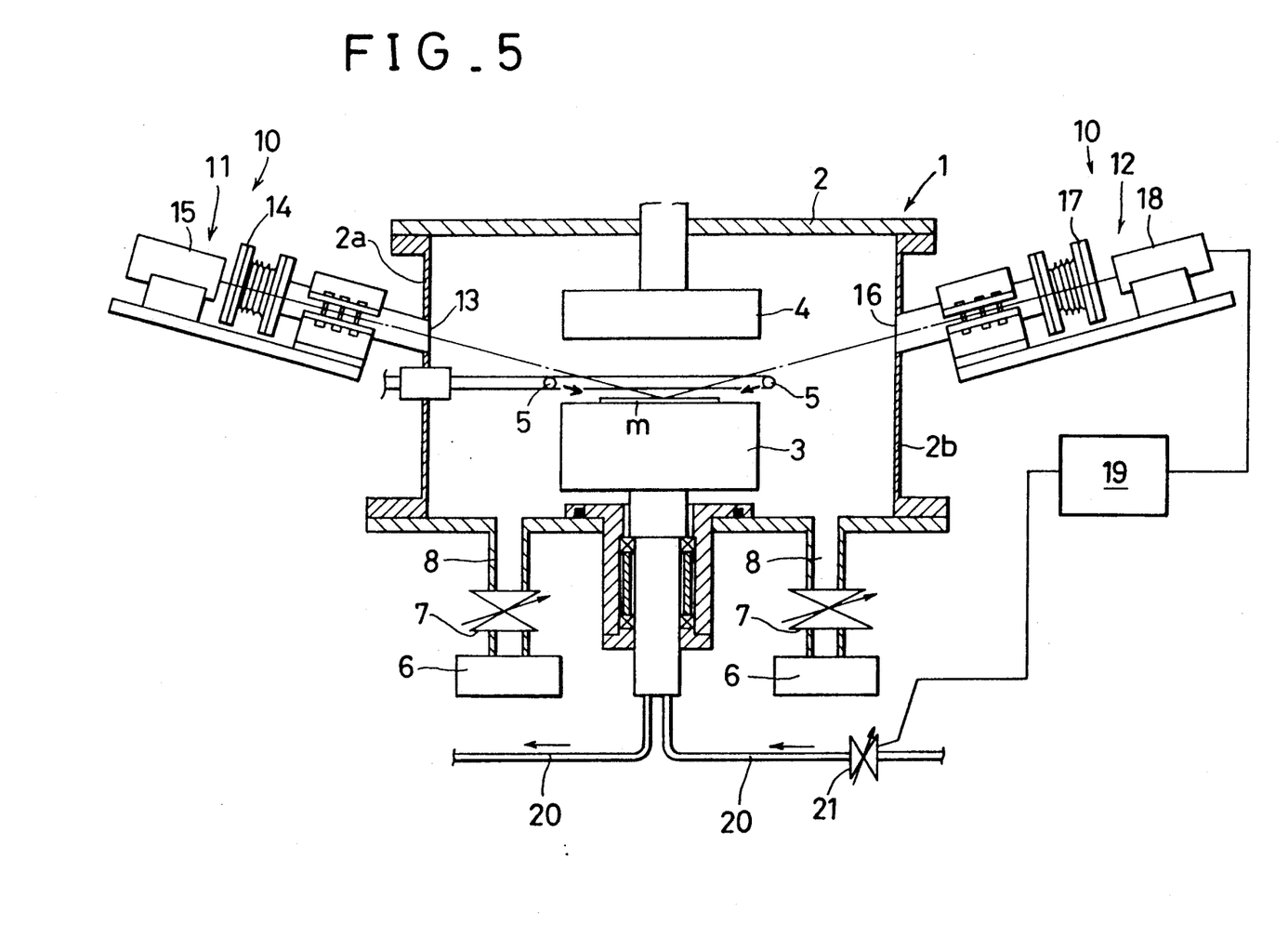
FIG. 5 is a sectional view of a gas phase synthesizing apparatus of another embodiment of this invention.

FIG. 5 shows another embodying example of this invention apparatus for gas phase synthesis. The difference between the apparatus as shown in FIG. 5 and the apparatus as shown in FIG. 1 is explained hereinbelow.

The synthesizing chamber 2 is connected to an evacuating system 6 such as vacuum pumps or the like via exhausting pipes 8 which are provided with regulating valves 7.

The light receiving member 18 is connected to a computer-equipped data processing system 19 which performs the ellipsometric analysis by analyzing the changes in polarization before and after the reflection of the light on the surface of the substrate m. The substrate electrode 3 is connected to a circulation pipe 20 for circulating therein cooling water for cooling the electrode 3. On an upstream side of the circulation pipe 20, there is provided a flow rate control device 21 for controlling the flow rate of cooling water to be circulated within the substrate electrode 3. The flow rate control device 21 and the data processing system 19 are communicated with each other so that the flow rate adjustment of the cooling water in the circulation pipe 20 can be made by adjusting the opening degree of the flow rate control device 21 depending on the control voltage to be output from the data processing system 19.

The other reference numerals are the same as those of FIG. 1 and, therefore, they are not repeated here.

By using the apparatus as shown in FIG. 5, the pressure, i.e., the vacuum degree inside the synthesizing chamber 2 can be maintained in a predetermined value by opening or closing the regulating valve 7. Further, even if the substrate m becomes higher in temperature due to the electric discharging during film formation, it can be cooled by circulating cooling water through the cooling pipe 20. Furthermore, by providing the circulating pipe 20 with the flow rate control device 21 which is in communication with the data processing system 19, the substrate m can be maintained at a predetermined temperature to suit the formation of the thin film having a desired density N of nucleation, even though the temperature of the substrate m may be raised due to the electric discharging during the formation of the thin film.

An explanation is made about an example of forming a diamond thin film using the gas phase synthesizing apparatus shown in FIG. 5 while adjusting the temperature of the substrate m during film formation.

Two (2) % methane gas diluted by hydrogen was charged into the synthesizing chamber 2 through the reactive gas discharging pipe 5. By operating the regulating valve 7, the synthesizing chamber 2 was maintained at 27 kPa. While maintaining the substrate m of silicon at respective temperatures of 800° C., 850° C., 900° C., 950° C and 1000° C., the discharging electric current of 5 A/cm$^2$ was discharged to form the diamond thin film on the substrate m. At each temperature of the substrate m, the density N of nucleation of diamond was examined. The results are given in FIG. 6.

The density of nucleation was obtained in the following manner through the changes in the ellipsometric parameter angles.

The difference $\delta\Psi$ was calculated between the value $\Psi a$ of the parameter angle $\Psi$ which is measured when the parameter angle $\Delta=140°$ with the growth of nuclei and the value $\Psi_b$ of the parameter angle $\Psi$ at the time of starting the film formation. Then, another difference $\delta\Psi$ between the parameter angles, which was obtained by a similar calculation method as a result of simulation as shown in FIG. 3, was compared with the former value for determining the density of nucleation.

Figure 6:
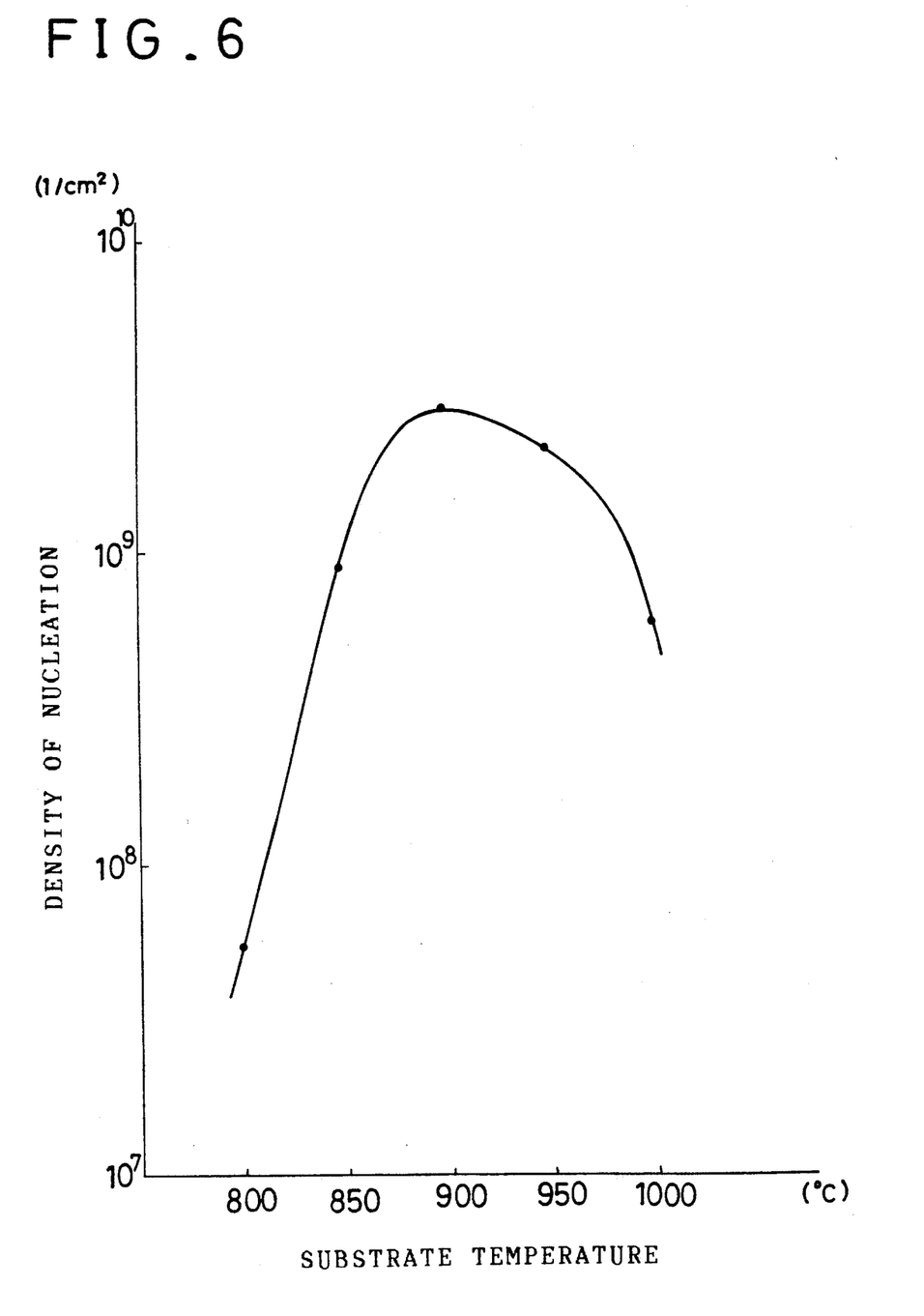
FIG. 6 is a graph showing the relationship between the substrate temperature and the density of nucleation.

As can be seen in FIG. 6, it has been found that the density N of nucleation varies with the substrate temperature and that a maximum value can be obtained at a certain temperature. Since these results vary with the film formation conditions and the arrangement of the apparatus, this kind of method by means of monitoring is necessary in order to form the film while controlling the density of nucleation.

In order to form the film at as low a temperature as possible based on the experimental results obtained in the above monitoring so that the density N of nucleation becomes $10^9$/cm$^2$ or more, the diamond film can be formed by synthesis on the substrate m while controlling the opening degree of the flow rate control device 21 by the control voltage which is output from the computer-equipped data processing system 19 for polarization monitoring.

In this manner, there can be synthesized on the substrate m the thin diamond film having a density of nucleation of $10^9$/cm$^2$ or more while maintaining the substrate temperature as low as possible in each film formation operation.

It can be considered as another method of controlling the density of nucleation, that the evaluation of the density of nucleation is carried out during the film formation and that the film formation in the course of the operation is stopped or the controlling of the conditions in the following batch operation is carried out. This kind of method is effective in an actual manufacturing stage. In other words, since the apparatuses become complicated and on a large scale in the manufacturing facility and, as a result, it is estimated that the accuracy of ellipsometric measurement generally becomes poor. If the accuracy of ellipsometric measurement becomes poor, the size of the diamond nuclei of minimum requirement in accurately obtaining the density of nucleation, becomes large. Then, there are cases where it is too late for the control in the batch operation which is then in progress. Therefore, as an effective method of improving the efficiency of production, the following may be done. Namely, at a time when it has been found through the ellipsometric measurement that the density of nucleation has fallen short of the required conditions, the production may be stopped at as early a stage as possible to remove the product of poor quality so that a step can be taken to change the film formation conditions of the next batch of production.

In the above-described example, the difference value $\delta\Psi$ of the parameter angles $\Psi$ before and during the film formation was used in obtaining the density of nucleation. Though this method is simple, the following method may also be used to obtain a more accurate density of nucleation. Namely, there is obtained by calculation a curve which most closely approaches the curve which represents the changes in the empirically obtained $\Psi$ value and $\Delta$ value of parameter angles, i.e., a locus of points ($\Psi,\Delta$) of parameter angle values on the coordinates by varying parameters as the density N of nucleation, the height D of the nuclei and so on.

In other words, the angle $\Delta$ and the angle $\Psi$ have parameters such as the density N of nucleation, the height D of the nuclei, the refractive index $n_s$ of the substrate, the the refractive index $n_i$ of the boundary layer, and the thickness $d_i$ of the boundary layer and the like. If the nucleus height D of the nuclei is changed among these parameters, a curve can be drawn. A curve that can be naturally determined by a combination of values of parameters to be selected from among the remaining parameters, is compared with the experimental data by, e.g., a method of least squares. The N value then obtained becomes the density of nucleation.

The film forming conditions during the film forming operation are not limited to the above-described adjustments of the substrate temperature. Instead, the concentration of hydrocarbon in the synthesis gas to be introduced into the synthesizing chamber 2, the pressure inside the synthesizing chamber 2, the discharging electric current, or the like may be set to an appropriate value in response to the density of nucleation of the diamond thin film to be formed on the substrate m.

As shown in FIG. 5, if the synthesizing chamber 2 is connected to the evacuating pump 6 via regulating valves 7, the vacuum degree inside the synthesizing chamber 2 can be easily maintained at a desired pressure by the operation of the regulating valves.

As described above, according to the method of gas phase synthesis of this invention, it is possible to measure and analyze the polarization state of the light as reflected from the substrate to grasp the density of nucleation. It is therefore possible evaluate and control the density of nucleation during the growth of diamond and therefore to accurately control the density of nucleation depending on the requirements of the film.

In addition, by adjusting the substrate temperature during the formation of the film, it is possible to form a film having a desired density of nucleation.

According to gas phase synthesizing apparatus of this invention, it is possible to provide an apparatus in which the density of nucleation can be grasped by measuring and analyzing the polarization state of the light as reflected from the substrate to facilitate the control of the film formation of a predetermined density of nucleation and in which the diamond thin film having a very accurately controlled density of nucleation can be easily formed on the substrate.

Further, by connecting the evacuating system to the synthesizing chamber, it becomes possible to easily maintain the synthesizing chamber to a desired pressure.

Still further, by providing the synthesizing chamber with the substrate electrode which is equipped with the flow rate control device for cooling water, it becomes easy to adjust the substrate temperature during the film formation.

By connecting the flow rate control device to the data processing system, it becomes easy to control the amount of the cooling water which flows through the cooling water circuit.

It is readily apparent that the above-described method has the advantage of wide commercial utility. It should be understood that the specific form of the invention hereinabove described is intended to be representative only, as certain modifications within the scope of these teachings will be apparent to those skilled in the art.

Accordingly, reference should be made to the following claims in determining the full scope of the invention.

What is claimed is:

1. A method of gas phase synthesis of a material comprising the steps of measuring, by ellipsometry, optical properties of a surface of a sample on which a film is being formed during the formation of the film, and of evaluating the density of nucleation from changes in the ellipsometric parameter angles during formation of the film.

2. A method of gas phase synthesis according to claim 1, wherein the density of nucleation is controlled by adjusting film forming synthesis conditions during formation of the film.

3. A method of gas phase synthesis according to claim 1, wherein the density of nucleation is controlled by adjusting a temperature of the sample substrate.

4. A method of gas phase synthesis according to any one of claims 1 through 3, wherein a film to be synthesized is diamond.

5. In a method for the gas phase synthesis of a material in a vacuum chamber having a substrate electrode provided with a cooling means, a discharge electrode and a gas inlet means, the improvement comprising determining the density of nucleation of said material deposited upon said substrate by measuring the ellipsometric parameter angles $\Psi$ and $\Delta$ during deposition of a material and adjusting at least one of the pressure within the chamber and a temperature of the substrate to obtain the desired density of nucleation.

6. In a method of gas phase synthesis according to claim 5, the improvement wherein the ellipsometric parameter angles $\Psi$ and $\Delta$ are measured by projecting polarized light through a window into said vacuum chamber into said material formed upon said substrate and analyzing the light reflected from said material.

7. A method of manufacturing a material comprising thin films which grow in the form of nuclei, said method comprising the steps of:
   measuring by ellipsometry conditions of a surface of said material during growing of said films; and
   evaluating a density of nucleation from a value of said ellipsometry or changes of said value, said evaluation being made during growth of said nuclei.

* * * * *

UNITED STATES PATENT AND TRADEMARK OFFICE
CERTIFICATE OF CORRECTION

PATENT NO. : 5,276,503

DATED : January 4, 1994

INVENTOR(S) : Hayashi et al

It is certified that error appears in the above-indentified patent and that said Letters Patent is hereby corrected as shown below:

On the title page, item [73], "Ninon Shinku Gijutsu Kabushiki Kaisha" should be —Nihon Shinku Gijutsu Kabushiki Kaisha—.

On the title page, item [30], Priority Date, delete "Oct. 9, 1991 [JP] Japan 3-262318"

Column 8, line 51, claim 5, "the" should be —a—.
Column 8, line 58, claim 6, "into" should be —onto—.

Signed and Sealed this

Twenty-fifth Day of October, 1994

Attest:

BRUCE LEHMAN

*Attesting Officer*       *Commissioner of Patents and Trademarks*